United States Patent
Smith

(10) Patent No.: US 12,201,852 B2
(45) Date of Patent: Jan. 21, 2025

(54) DELIVERY OF RADIOTHERAPY

(71) Applicant: Elekta Limited, Crawley (GB)

(72) Inventor: Adrian Smith, Crawley (GB)

(73) Assignee: Elekta Limited, Crawley (GB)

( * ) Notice: Subject to any disclaimer, the term of this patent is extended or adjusted under 35 U.S.C. 154(b) by 325 days.

(21) Appl. No.: 17/593,883

(22) PCT Filed: Mar. 27, 2020

(86) PCT No.: PCT/EP2020/058847
§ 371 (c)(1),
(2) Date: Sep. 27, 2021

(87) PCT Pub. No.: WO2020/193790
PCT Pub. Date: Oct. 1, 2020

(65) Prior Publication Data
US 2022/0168593 A1  Jun. 2, 2022

(30) Foreign Application Priority Data
Mar. 27, 2019  (GB) ...................................... 1904255

(51) Int. Cl.
*A61N 5/10* (2006.01)
(52) U.S. Cl.
CPC ......... *A61N 5/1049* (2013.01); *A61N 5/1037* (2013.01); *A61N 5/1038* (2013.01); *A61N 5/1071* (2013.01); *A61N 5/1081* (2013.01)
(58) Field of Classification Search
CPC .. A61N 5/1049; A61N 5/1037; A61N 5/1038; A61N 5/1071; A61N 5/1081;
(Continued)

(56) References Cited

U.S. PATENT DOCUMENTS 8,835,878 B2 * 9/2014 Nord .................... A61N 5/1049
378/68
2010/0166145 A1  7/2010 Umekawa et al.
(Continued)

FOREIGN PATENT DOCUMENTS

EP          2407206 A1    1/2012
WO   WO-2007014090 A2    2/2007
(Continued)

OTHER PUBLICATIONS

"International Application Serial No. PCT/EP2020/058847, International Search Report dated Apr. 4, 2020", (May 4, 2020), 5 pgs.
(Continued)

*Primary Examiner* — Courtney D Thomas
(74) *Attorney, Agent, or Firm* — Schwegman Lundberg & Woessner, P.A.

(57) ABSTRACT

A method of controlling a radiotherapy device, a computer readable medium and a radiotherapy device are disclosed. The radiotherapy device includes a radiation source coupled to a rotation means. The method includes applying radiation to a subject using the radiation source and rotating the radiation source around the subject using the rotation means according to a first fixed rotation scheme. The method further includes, during execution of the first fixed rotation scheme, determining that the subject is in a suboptimal position, pausing application of the radiation by the radiation source and logging a first angle of rotation of the radiation source at which application of the radiation is paused.

20 Claims, 6 Drawing Sheets

(58) Field of Classification Search
CPC .......... A61N 5/1064; A61N 5/1068; A61N 2005/0627; A61N 2005/107; A61B 5/113; A61B 6/541
See application file for complete search history.

(56) References Cited

U.S. PATENT DOCUMENTS

| | | |
|---|---|---|
| 2010/0290586 A1 | 11/2010 | Friedrich |
| 2018/0056090 A1 | 3/2018 | Jordan et al. |
| 2018/0117358 A1 | 5/2018 | Nord et al. |

FOREIGN PATENT DOCUMENTS

| | | | | |
|---|---|---|---|---|
| WO | WO-2016187319 A1 | | 11/2016 | |
| WO | WO-2019160958 A1 | * | 8/2019 | ............. A61B 6/032 |

OTHER PUBLICATIONS

"International Application Serial No. PCT/EP2020/058847, Written Opinion dated Apr. 4, 2020", (May 4, 2020), 8 pgs.
"United Kingdom Application Serial No. 1904255.2, Examination Report dated Sep. 20, 2019", (Sep. 20, 2019), 6 pgs.
"Chinese Application Serial No. 202080040097.2, Office Action dated Nov. 15, 2023", w English Translation, (Nov. 15, 2023), 11 pgs.
"European Application Serial No. 20 715 363.6, European Search Report dated Jan. 29, 2024", (Jan. 29, 2024), 5 pgs.
"British Application No. 1904255.5, Examination Report dated Jul. 2, 2021", (Jul. 2, 2021), 3 pgs.
"Chinese Application Serial No. 202080040097.2, Office Action dated May 30, 2024", w English Translation, (May 30, 2024), 14 pgs.

* cited by examiner

DELIVERY OF RADIOTHERAPY

PRIORITY APPLICATIONS

This application is a U.S. National Stage Filing under 35 U.S.C. § 371 from International Application No. PCT/EP2020/058847, filed on Mar. 27, 2020, and published as WO2020/193790 on Oct. 1, 2020, which claims the benefit of priority to United Kingdom Application No. 1904255.5, filed on Mar. 27, 2019; the benefit of priority of each of which is hereby claimed herein, and which applications and publication are hereby incorporated herein by reference in their entireties.

This disclosure relates generally to the delivery of radiotherapy, and in particular to controlling the delivery of radiotherapy.

BACKGROUND

Radiotherapy uses ionising radiation to treat a human or animal body. In particular, radiotherapy is commonly used to treat tumours within the human or animal body. In such treatments, the cells forming part of the tumour are irradiated by ionising radiation in order to destroy or damage them. However, in order to apply a prescribed dose of ionising radiation to a target location or target region, such as a tumour, the ionising radiation will typically also pass through healthy tissue of the human or animal body. Therefore, radiotherapy has the desirable consequence of irradiating and damaging a target region, but can also have the undesirable consequence of irradiating and damaging healthy tissue. It is desirable to minimise the dose received by healthy tissue in radiotherapy treatment.

Modern radiotherapy treatment uses techniques to reduce the radiation dose to healthy tissue and thereby provide a safe treatment. For example, a standard approach to minimising a radiation dose received by healthy tissue surrounding a target region is to direct the radiation towards the target region from a plurality of different angles, for example by rotating a source of radiation around the patient by use of a rotating gantry. In this case, the angles at which radiation is applied are selected such that each beam of radiation passes through the target region. In this way, a cumulative radiation dose may be built up at the target region over the course of a treatment delivery in which the radiation source rotates through a certain angle. However, since the radiation is applied from a plurality of different angles, the same, high, cumulative radiation dose is not built up in the healthy tissue because the specific healthy tissue the radiation passes through varies with angle. Therefore, a unit volume of the healthy tissue receives a reduced radiation dose relative to a unit volume of the target region.

However, movement of a patient can affect the dose applied to different regions of the patient's body. For example, movement of the patient can cause movement of a tumour and thus the dose applied to the target region is decreased and the dose applied to the healthy tissue is increased. In other words, if a patient moves during or prior to radiotherapy treatment, this can cause a high cumulative dose to build up in a region of healthy tissue instead of in a target region. This can reduce the effectiveness of the radiotherapy for treating the target region and can cause damage to otherwise healthy tissue.

There are various reasons why a patient may move during or prior to radiotherapy treatment. Gross or large-scale movements of a patient may include the patient shifting position or sitting up. Discrete movements of the patient may include the patient coughing or sneezing. In some cases, large-scale movements may correspond to discrete movements. The patient may also undergo cyclical, physiological movement. For example, breathing of the patient can cause quasiperiodic movement of the patient that may move a position of a target region, such as a tumour, with respect to time.

To address this, known techniques include training a patient's breathing or asking the patient to hold their breath during radiotherapy treatment. In such techniques, the patient's breathing is adjusted based on the requirements of the radiotherapy. However, this may be uncomfortable or impossible for certain patients, and often restricts the time during which radiation can be applied.

In other known techniques, a treatment delivery may be stopped when a patient's breathing causes sufficient movement of the patient. For example, in some prior systems, the movement of the patient as they breathe in or out may be sensed by any of a variety of known sensors, and radiation is only applied during a certain part of the patient's breathing cycle. The patient's breathing cycle may be divided, for example, into two regions: a first, optimal region in which radiation should be applied, and a second, suboptimal region in which radiation should not be applied for safety reasons. In response to sensing that the patient's breathing cycle has entered the suboptimal region, the rotation of the gantry and the application of radiation is halted such that the treatment delivery is stopped.

However, the halting of the rotation may occur at some time after it is sensed that the patient's breathing cycle has entered the suboptimal region. This may be due to, for example, the inertia of the rotating gantry. In other words, due to the considerable mass of the gantry, it may not be possible to stop rotation instantly. This may mean that the rotation continues over some non-zero angle before the gantry comes to a halt. Therefore, after halting rotation of the gantry and the radiation means/radiation source, the gantry and the radiation means may be at an angle greater than the angle at which the patient's breathing cycle entered the suboptimal region. Because of this, it is typically necessary to reverse rotation of the gantry and the radiation means. This halting and reversal of rotation may cause delays in treatment and patient throughput.

In addition, beginning a further rotation of the gantry in order to apply further radiation involves accelerating the gantry back up to the desired speed of rotation. During this acceleration, the amount of radiation applied at each angle of rotation may not be constant and consistent, which can cause dosimetric errors. In this way, a dose applied to a target region may be lower than desired and/or a dose applied to a healthy region may be higher than desired. In other words, known techniques lead to dosage inaccuracies during radiotherapy treatment.

It would be advantageous to minimise the dose received by healthy tissue during radiotherapy treatment. It would also be advantageous to align the dose received by a target region with an intended, e.g. prescribed, dose for the target region more precisely. It would also be advantageous to increase the speed of radiotherapy treatment and increase patient comfort during treatment.

The present invention seeks to address these and other disadvantages encountered in the prior art by providing improved delivery of radiotherapy.

SUMMARY

An invention is set out in the claims.

According to an aspect, there is provided a method of controlling a radiotherapy device. The radiotherapy device comprises a radiation source coupled to a rotation means. The method comprises: applying radiation to a subject using the radiation source and rotating the radiation source about around the subject using the rotation means according to a first fixed rotation scheme. The method also comprises, during execution of the first fixed rotation scheme: determining that the subject is in a suboptimal position, pausing application of the radiation by the radiation source; and logging a first angle of rotation of the radiation source at which application of the radiation is paused.

The method may be a computer-implemented method. The pausing of the application of the radiation may be in response to the determining that the subject, or patient, is in the suboptimal position. Determining that the patient is in a suboptimal position may be based on patient position and/or movement information supplied by a patient movement sensor.

According to an aspect, a computer readable medium is provided comprising computer executable instructions which, when executed by a processor, cause the processor to perform the method of any of the disclosed methods.

According to an aspect, a radiotherapy device comprising a radiation source coupled to a rotation means is provided. The device is configured to perform any of the disclosed methods. In particular, the device may be configured to perform the disclosed methods by virtue of a computer readable medium which, when executed by a processor, cause the device to apply radiation to a subject using the radiation source, and rotate the radiation source around the subject using the rotation means according to a first fixed rotation scheme. During execution of the first fixed rotation scheme, the device determines that the subject is in a suboptimal position, pauses application of the radiation by the radiation source, and logs a first angle of rotation of the radiation source at which application of the radiation is paused.

FIGURES

Specific embodiments are now described, by way of example only, with reference to the drawings, in which.

DETAILED DESCRIPTION

Instead of halting rotation of the gantry and radiation source in response to determining that a subject or patient is in a suboptimal position, as in methods of the prior art, in presently disclosed methods the application of radiation is paused but rotation of the radiation source continues in accordance with a fixed rotation scheme. The angle at which radiation has halted or paused is logged. After the fixed rotation scheme and/or a treatment delivery has ended, it can be determined whether the dose applied to the target region is sufficient according to the treatment plan. If the applied dose is insufficient, treatment can be continued via another fixed rotation scheme and/or treatment delivery to 'fill in the gaps', i.e. to apply the radiation to the subject at those angles at which radiation was not applied during the first rotation scheme and/or treatment delivery. Thus, the prescribed dose is built up at the target region while radiation dose to healthy tissue is minimised. At the same time, the speed of radiotherapy treatment and patient comfort during treatment are increased.

In the following, a method, apparatus and computer-readable medium for delivery of radiotherapy are provided. In the following, application of radiotherapy to a patient will be referred to in most detail in order to provide clarity of explanation. Such use of the term patient should not be interpreted to limit application of the present disclosure. The present disclosure provides means that can be used to apply radiotherapy to any subject. The terms patient and subject may be used interchangeably herein.

In the following, breathing of a patient is referred to in most detail in order to provide clarity of explanation. However, the present disclosure is applicable to any voluntary or involuntary movement of a subject, including due to a breathing or respiratory cycle, a cardiac cycle, coughing, sneezing, and/or other movements of a subject.

Figure 1A:
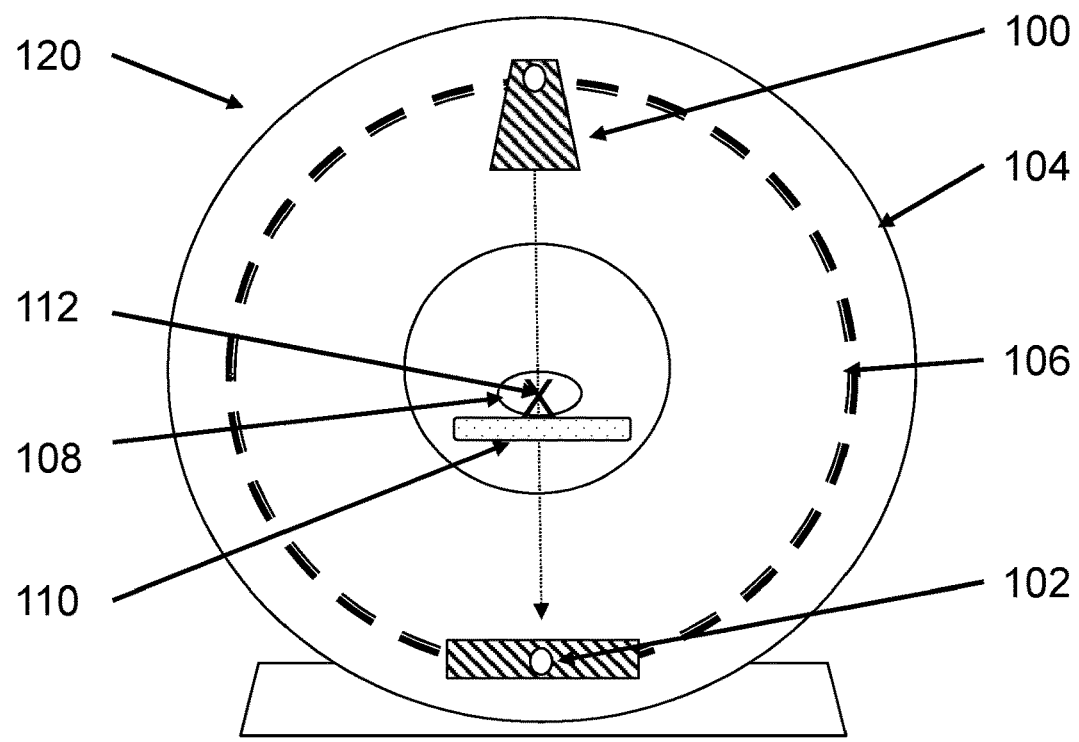
FIGS. 1a and 1b depict a radiotherapy device according to the present disclosure.
Figure 1B:
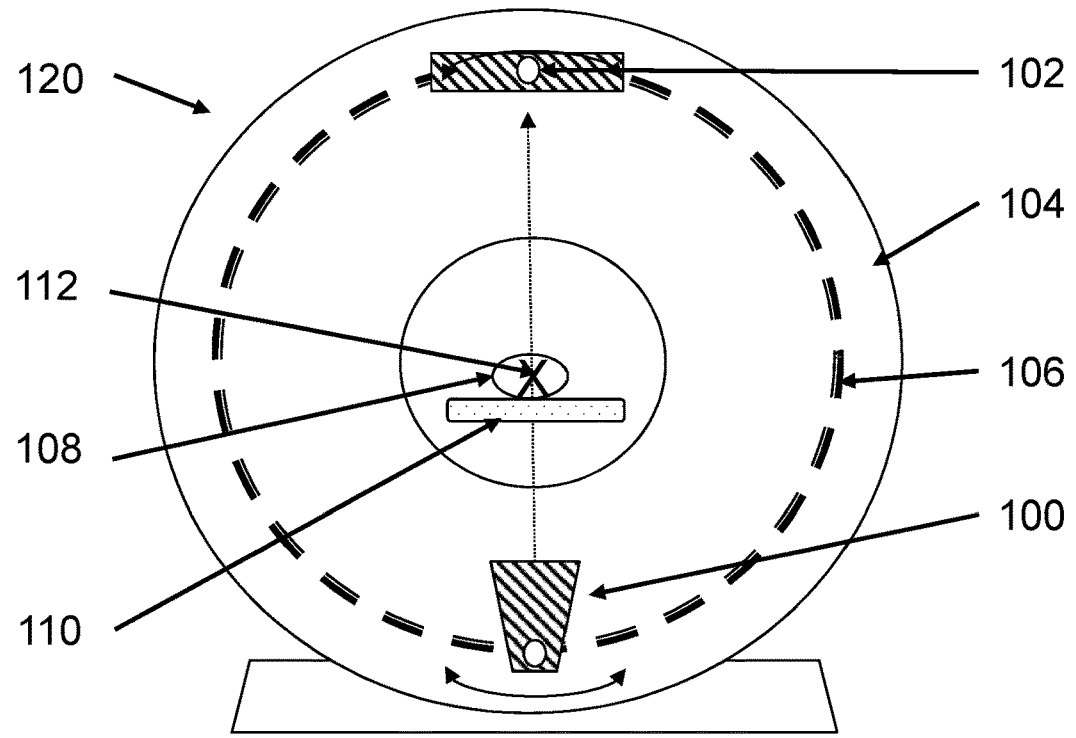

FIG. 1a and FIG. 1b depict a radiotherapy apparatus according to the present disclosure. The arrangement described should be considered as providing one or more examples of a radiotherapy device 120 and it will be understood that other arrangements are possible and can be used to perform the methods described herein. The figures show a cross-section through a radiotherapy device 120 comprising a radiation source 100 and a detector 102 attached to a gantry 104. The gantry may comprise a circular support track 106. The radiation source 100 and detector 102 may be arranged diametrically opposed to one another. The radiation source 100 and the detector 102 may be fixed to the gantry 104 and may rotate with the gantry 104. FIG. 1a and FIG. 1b also show a patient 108 lying on a support surface 110. As the radiation is delivered to the patient, for example according to a treatment plan, the radiation source 100 and the detector 102 may rotate together with the gantry 104 and/or around the circular support track 106 such that they are always arranged 180° from one another. The radiation source 100 directs radiation towards the patient 108 from various angles around the patient 108 in order to spread out the radiation dose received by healthy tissue to a larger region of healthy tissue while building up a prescribed dose of radiation at a target region. In FIG. 1a, the radiation source 100 is at the top of the radiotherapy device 120 and the detector 102 is at the bottom of the radiotherapy device 120. FIG. 1b shows both components having been rotated 180°. The rotation may to be any angle. In some cases, the components may be rotated a further 180° such that a total rotation of 360° is achieved and the orientation of the components corresponds to that in FIG. 1a once more.

As shown in FIG. 1a and FIG. 1b, radiation may be emitted in a plane which is perpendicular to the axis of rotation of the radiation source 100. Thus, radiation may be delivered to a radiation isocentre 112 at the centre of the gantry 104 regardless of the angle to which the radiation head is rotated around the gantry 104.

A treatment delivery may comprise rotation of the radiation source 100 and application of radiation by the radiasource 100, for example according to a treatment plan. A treatment delivery may comprise a treatment arc. In a treatment delivery, the rotation of the radiation source 100 may be through a predetermined angle. In some examples, a treatment delivery may comprise more than one rotation around a patient 108, for example comprising a total rotation through more than 360°. The rotation of the radiation source 100 may be according to a fixed rotation scheme. Rotation of the radiation source 100 may comprise execution, operation or implementation of the fixed rotation scheme. The fixed rotation scheme may comprise a predetermined rotation of the radiation source 100 that is not altered during the treatment delivery. For example, the fixed rotation scheme may comprise continuous rotation, rotation at a constant rate, rotation at an increasing rate, rotation at a decreasing rate and/or discrete periods of rotation interspersed with periods in which the radiation source 100 is stationary. The discrete periods of rotation may be to a series of discrete orientations relative to the patient 108. However, the fixed rotation scheme is fixed in that it is not adjusted during a treatment delivery. The fixed rotation scheme may be suitable for applying a certain radiation dose to a subject, for example according to a treatment plan.

According to prior techniques which halt the application of radiation and halt rotation of the radiation source in response to determining that a particular patient has moved to a certain degree, a radiotherapy session/treatment for the particular patient is likely to consist of several treatment deliveries due to halts or interruptions resulting from movement of the patient. In this scenario, each treatment delivery begins with the commencement of rotation of the radiation source, and ends when rotation of the radiation source is halted.

It can be seen from FIG. 1a and FIG. 1b that, if the patient 108 remains stationary during a treatment delivery, a cumulative radiation dose will build up at the radiation isocentre 112 since the radiation will pass through this radiation isocentre 112 throughout the rotation. The patient and the radiotherapy device 120 are arranged such that the radiation isocentre 112 coincides with a target region or a target location, for example a location of a tumour. However, if the patient moves during a treatment delivery, the radiation isocentre 112 and target region will no longer coincide.

For discrete patient motion, such as may be caused by coughing or sneezing of the patient 108, a displacement of the radiation isocentre 112 relative to the target region may change by a discrete amount. For quasiperiodic patient motion, such as may be caused by breathing of the patient 108, a displacement of the radiation isocentre 112 relative to the target region may vary quasiperiodically. As used herein, the term quasiperiodic may be used to refer to a motion or cycle that has a component that varies periodically, and that may have an unpredictable or irregular component. In other words, the term may be used to refer to a cycle that has a pattern of recurrence, but that may comprise variations in amplitude and/or period.

Different schemes for applying radiotherapy to a patient 108 are known. In intensity modulated radiotherapy (IMRT), a radiation beam is shaped to correspond closely to a distribution of unhealthy tissue. IMRT may therefore be described as conformal radiotherapy treatment. The shaping of the radiation beam can be performed using a collimator such as a multileaf collimator, the leaves of which can be moved independently in order to provide a variety of different beam shapes. Movement of the leaves of the multileaf collimator may weaken the requirement that the target region coincides with radiation isocentre 112 due to the additional flexibility that is provided. In IMRT, radiation may be applied from multiple, discrete beam angles. According to another scheme for applying radiotherapy, in volumetric modulated arc therapy (VMAT), radiation is continuously applied while a radiation source 100 progresses through an arc trajectory. The beam of radiation may be reshaped and/or varied in intensity during the rotation such that doses are applied dynamically during gantry rotation. Therefore, this scheme may be more time-efficient than IMRT. The presently disclosed methods are applicable with IMRT and with VMAT.

Figure 2:
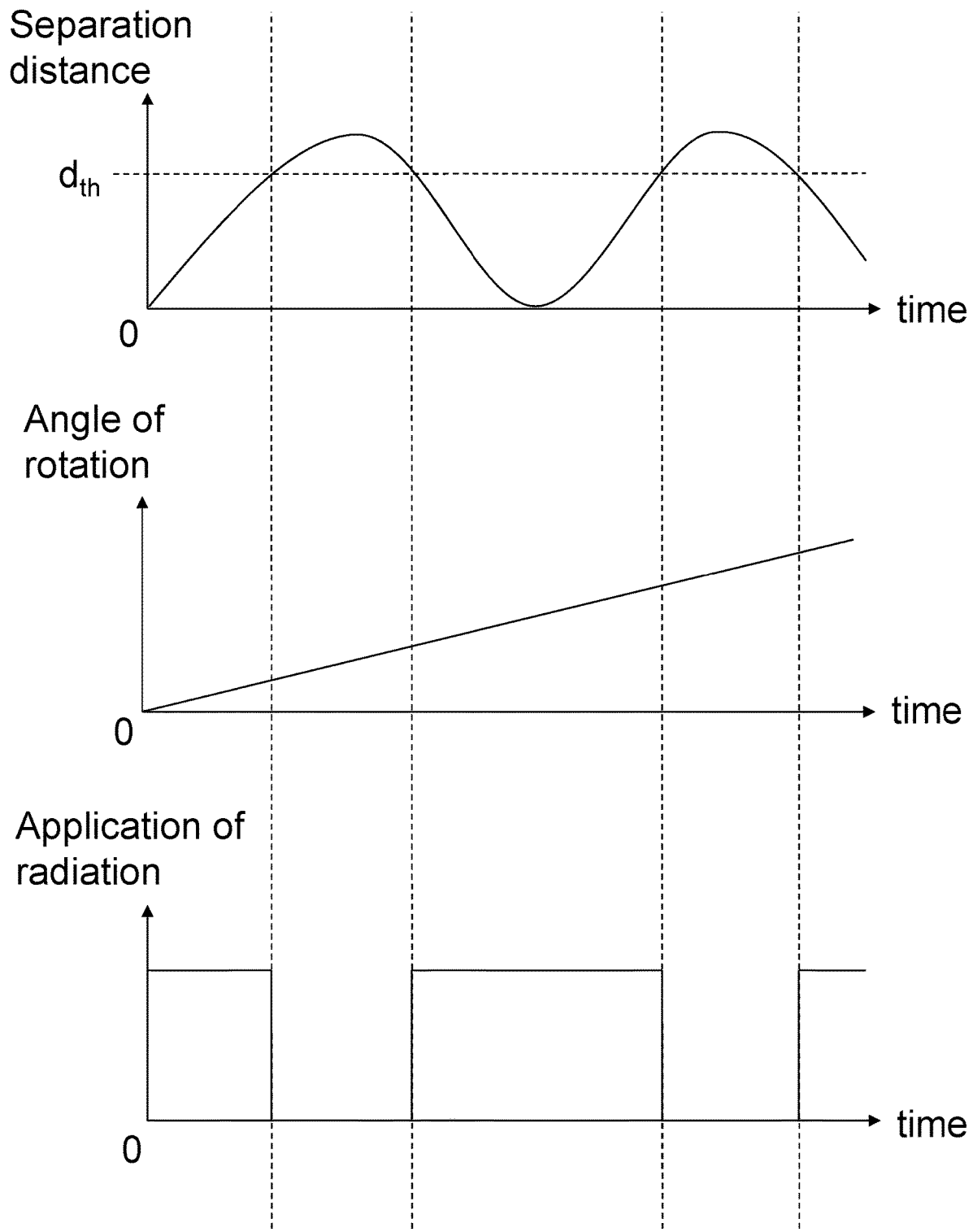
FIG. 2 depicts parameters of radiotherapy treatment according to the present disclosure.

FIG. 2 depicts parameters of radiotherapy treatment according to the present disclosure. These parameters are examples intended to illustrate the principles of the present disclosure and do not limit the present disclosure to the exemplary parameters depicted.

At the top of FIG. 2, a plot of separation distance as a function of time is shown. Herein, separation distance may be taken to define a displacement or an absolute distance between a target location within the patient 108 and a radiation isocentre 112. The time axis defines the time elapsed during a particular treatment delivery. As can be seen from the plot, the separation distance may vary with time quasiperiodically. This may correspond to a quasiperiodic motion of a patient 108. In particular, this may correspond to a quasiperiodic breathing cycle of the patient 108. For example, the peaks of the plot may correspond to times when the patient 108 has inhaled and the troughs of the plot may correspond to periods when the patient 108 has exhaled. In another example, the peaks of the plot may correspond to times when the patient 108 has exhaled and the troughs of the plot may correspond to times when the patient 108 has inhaled. This may depend on the extent to which the patient 108 had inhaled when a reference position of the target location relative to the radiation isocentre 112 was taken. The movement and/or breathing of the patient 108 may be determined based on any one or combination of suitable means, including but not limited to one or more cameras, movement sensors, accelerometers, chest bands and a button pressed by the patient 108. In some examples, the radiotherapy device is an MR-linac (Magnetic Resonance-linac), and further comprises an MR imaging device configured to track or monitor the movement of the patient or the patient anatomy (i.e. interior parts of the patient). In this implementation, the determination that the patient is in a suboptimal position is based on MR data supplied by the MR imaging device.

A horizontal dashed line on the plot at the top of FIG. 2 indicates a threshold separation distance $d_{th}$. The threshold separation distance $d_{th}$ may indicate a maximum separation distance that is acceptable. In other words, the threshold separation distance $d_{th}$ may indicate a separation distance at and below which radiotherapy is applied and above which radiotherapy is not applied. In still other words, the threshold separation distance may define the boundary between an optimal position of the patient, in which position the application of radiation meets safety requirements, and a suboptimal position of the patient. The threshold separation distance $d_{th}$ may be determined based on a treatment plan. The threshold separation distance $d_{th}$ may be determined based on a spatial distribution of a target region and/or a spatial distribution of healthy tissue and/or a planned dose to be applied. Vertical dashed lines separate time periods in which the separation distance is above the threshold separation distance $d_{th}$ and time periods in which the separation distance is at or below the threshold separation distance $d_{th}$.

The middle plot of FIG. 2 shows an angle of rotation as a function of time. Herein, angle of rotation may be taken to define an angle through which the radiation source 100 has rotated about a patient 108 using a rotation means. The rotation means may be described as a rotator or a rotation module. The time axis corresponds to the time axis in the plot of separation distance. The angle of rotation of the radiation source 100 may vary according to a fixed rotation scheme. As can be seen from the plot, in some examples, the angle of rotation of the radiation source 100 may increase continuously with time. In some examples, the angle of rotation of the radiation source 100 may increase linearly with time. Movement of the radiation means about the patient 108 may be continuous or substantially continuous. The example shown in FIG. 2 is provided for ease of explanation and should not be understood as limiting the disclosure.

As will be appreciated from FIG. 2, according to the present disclosure, rotation of the radiation source 100 may not be halted based on movement of the subject, for example due to breathing of a patient 108. In other words, according to the present disclosure, rotation of the radiation source 100 may not be halted when the separation distance between the target location and the radiation isocentre 112 is above the threshold separation distance $d_{th}$. Instead, rotation of the radiation source may continue according to the fixed rotation scheme.

The bottom plot of FIG. 2 shows an application of radiation as a function of time. Herein, application of radiation may be taken to define application of a radiation dose to a subject, for example to a patient 108, by the radiation source 100. The time axis corresponds to the time axis in the plot of separation distance and the time axis in the plot of angle of rotation. As can be seen from the plot, the radiation source 100 may alternate between applying a non-zero radiation dose and applying no (i.e. zero) radiation dose. While a single non-zero level of applied radiation is illustrated in the plot for ease of explanation, in some examples the applied radiation may be different at different times and/or may increase or decrease with time. In some examples, the zero radiation dose may be replaced with a low/reduced radiation dose. As can be seen with use of the vertical dashed lines, one or more time periods in which the radiation source 100 applies a non-zero radiation dose may correspond to one or more time periods in which the separation distance is at or below the threshold separation distance $d_{th}$. One or more time periods in which the radiation source 100 applies no radiation dose may correspond to one or more time periods in which the separation distance is above the threshold separation distance $d_{th}$.

Application of radiation by the radiation source 100 in some time periods but not in others may be achieved by gating of a radiation beam emitted by the radiation source 100. The radiation source 100 may comprise an electron source and a radiofrequency (RF) field source. The electron source may provide a source of electrons which generate a radiation dose to be delivered to the patient 108, for example by impacting a target. The RF field source may electromagnetically accelerate the electrons to a desired velocity suitable for providing the radiation dose. The radiation source 100 can be gated by controlling the electron source to be on or off and/or by controlling the RF field source to be on or off. In this manner, application of a radiation dose by the radiation source 100 can be controlled according to desired parameters, for example according to the time periods described above and/or the separation distance described above.

As can be seen from the discussion above, the present disclosure combines continuing rotation of a radiation source 100 according to a fixed rotation scheme, monitoring a position and/or movement of a patient 108, and applying radiation only when the patient 108 is not in a suboptimal position. This provides the combined benefits of limiting damage to healthy tissue, building up a cumulative radiation dose at a target location and increasing the speed of radiotherapy treatment. Since, according to the present disclosure, the radiation source 100 may not need to halt during a treatment delivery due to movement of the patient 108, the treatment delivery may take less time to complete. In addition, dosimetric errors due to reversing rotation and re-accelerating the radiation source 100 may be avoided.

Figure 3:
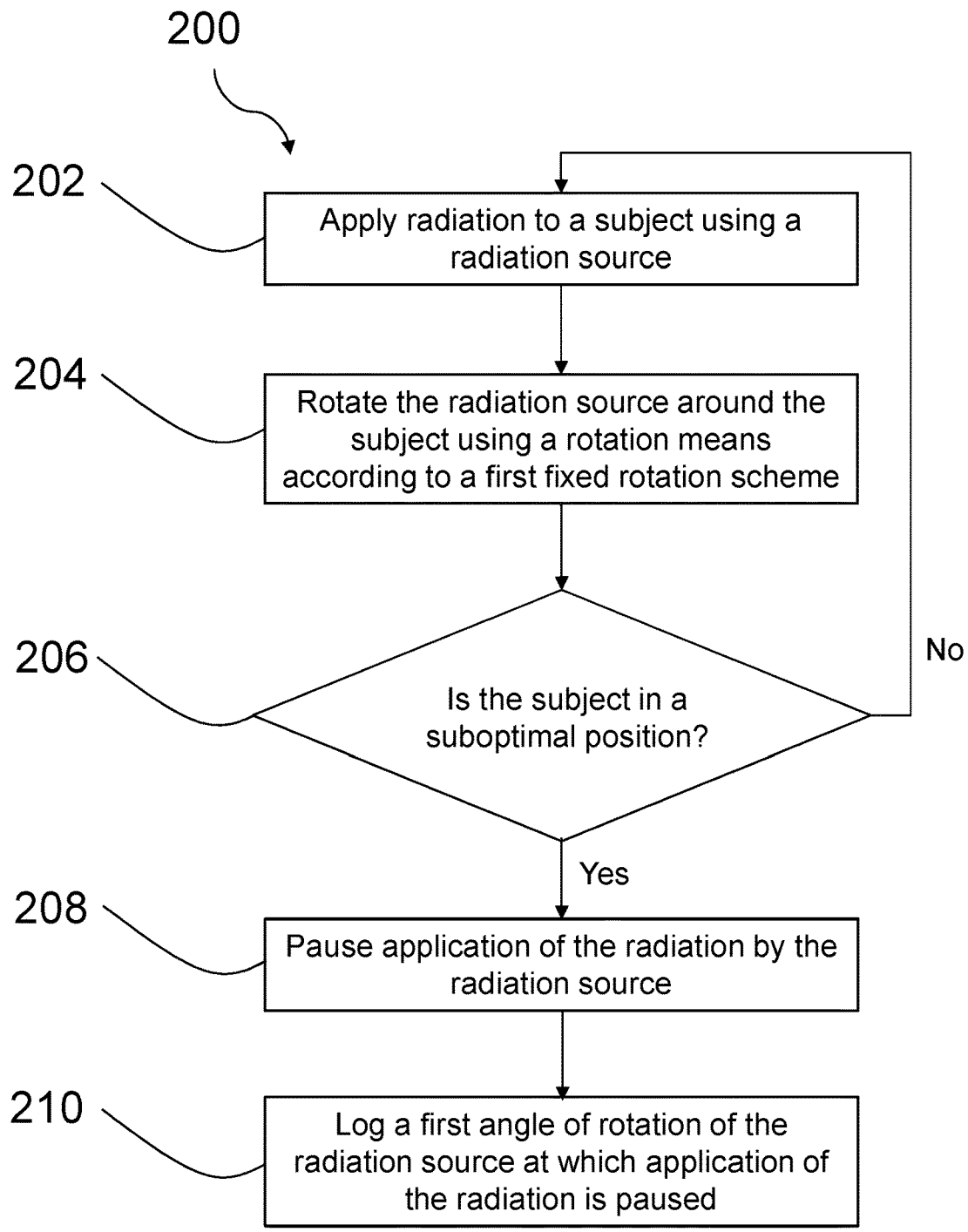
FIG. 3 depicts a method of controlling a radiotherapy apparatus according to the present disclosure.

FIG. 3 depicts a method 200 of controlling a radiotherapy device according to the present disclosure. The radiotherapy device may comprise corresponding features to the radiotherapy device depicted in FIG. 1a and FIG. 1b and/or described above.

In a step 202, radiation may be applied to a subject using a radiation source 100. The radiation source 100 may be configured to provide a radiation dose to a patient 108. The radiation source 100 may be configured to provide a planned dose to the patient 108 during a treatment delivery. Application of radiation to the patient 108 by the radiation source 100 may be based on a treatment plan.

In a step 204, the radiation source 100 may be rotated around the subject using a rotation means according to a first fixed rotation scheme. The subject may comprise a patient 108. The radiation source 100 may be fixed to a gantry 104. Rotation of the radiation source 100 by the rotation means may be effected by rotation of the gantry 104. Rotation of the gantry 104 may be effected by one or more motors or gears coupled to the gantry 104. The rotation means may comprise the one or more motors or gears configured to cause rotation of the gantry 104. Alternatively, the gantry 104 may be fixed and the radiation source 100 may be configured to move along the gantry 104 to effect rotation of the radiation source 100 around the subject. In this case, the rotation means may comprise one or more motors or gears configured to cause rotation of the radiation source 100. The radiation source 100 may be coupled or connected to the rotation means so as to enable rotation of the radiation source 100 by the rotation means. A speed of rotation and/or a rate of rotation of the radiation source 100 may be determined and/or controlled based on a treatment plan.

In a step 206, a determination may be made as to whether the subject is in a suboptimal position. The suboptimal position may be a position unsuitable for application of radiation by the radiation source 100. The suboptimal position may be a position in which the separation distance is greater than a threshold separation distance $d_{th}$. The determination 208 may be performed using various means. A position and/or movement of the subject, for example caused by or dependent on voluntary and/or involuntary movement of the subject, may be monitored. For example, the determination 206 may be made using one or more cameras viewing a patient 108. Alternatively, or in addition, the determination 206 may be made using motion sensors or accelerometers disposed on the patient 108. Alternatively, or in addition, the determination 206 may be made using a band around the patient's chest that expands during breathing in and contracts during breathing out. Alternatively, or in addition, the determination 206 may be made using a face mask worn by the patient 108. Alternatively, or in addition, the determination 206 may be made using a button pressed by the patient 108 at a certain point in their breathing cycle.

Alternatively, or in addition, the determination 206 may be made using MR data supplied by an MR imaging device. Various other techniques can be used in addition to or in place of the above exemplary techniques.

In some examples, the determination 206 as to whether the patient 108 is in a suboptimal position can be made based on a signal comprising movement data or breathing data for the patient 108. The breathing data may comprise at least one of an indication of an inhalation of the patient 108, an indication of an exhalation of the patient 108, an indication of a peak inhalation of the patient 108, an indication of a peak exhalation of the patient 108, a breathing rate of the patient 108 or a breathing period of the patient 108.

If the result of the determination 206 is that the patient 108 is not in a suboptimal position, the method may return to step 202. If the result of the determination 206 is that the patient 108 is in a suboptimal position, the method may continue to step 208.

In the step 208, application of the radiation by the radiation source 100 may be paused. The pausing of the application of the radiation may be performed using gating of the radiation source 100, as described above.

In a step 210, a first angle of rotation of the radiation source 100 at which application of the radiation is paused may be logged. The first angle of rotation may be logged in a log file.

Rotation of the radiation source 100 using the rotation means may be continued while the subject is in a suboptimal position, while the application of the radiation is paused and/or while the first angle of rotation is logged. In other words, since the radiation source rotates according to a fixed rotation scheme, the rotation may not be interrupted or halted in response to the subject being in a suboptimal position. The rotation of the radiation source 100 using the rotation means may be controlled using a controller communicatively coupled to the rotation means. The controller may be communicatively coupled to means for sensing a position and/or movement of the patient 108. The controller may comprise, or be described as, a computing device or a processor. The controller may be any machine capable of executing a set of instructions (sequential or otherwise) that specify actions to be taken by the radiotherapy apparatus and the components thereof as described herein.

The radiation source 100 may be configured to rotate continuously or substantially continuously during a treatment delivery. As used herein, the term continuously should not be interpreted to exclude any minimal breaks in rotation due to incremental rotation of the rotation means about a large series of discrete angles as part of its normal mode of rotation. Rather, the term continuously may indicate that there is no divergence from a fixed rotation scheme of the radiation source 100 during a treatment delivery via halts in a planned rotation, reversals of the planned rotation, and/or unplanned re-accelerations of the radiation source 100.

While the method set out in FIG. 3 is presented in a certain sequential order, this should not be taken to limit the method to the order presented. The various steps may be performed in a different order. Various steps may be performed at the same time or substantially at the same time. For example, the steps of applying 202 radiation using the radiation source 100 and rotating 204 the radiation source 100 may be performed at the same time or substantially at the same time. Alternatively, or in addition, the steps of pausing 208 application of the radiation by the radiation source 100 and logging 210 a first angle of rotation of the radiation source 100 may be performed at the same time or substantially at the same time. Herein, references to events occurring substantially at the same time may refer to events at least partially overlapping in time.

In the method depicted in FIG. 3, the patient 108 may not be in a suboptimal position at a start of the treatment or treatment delivery. For example, a determination may be made that the patient 108 is not in a suboptimal position before starting the treatment or treatment delivery.

Figure 4:
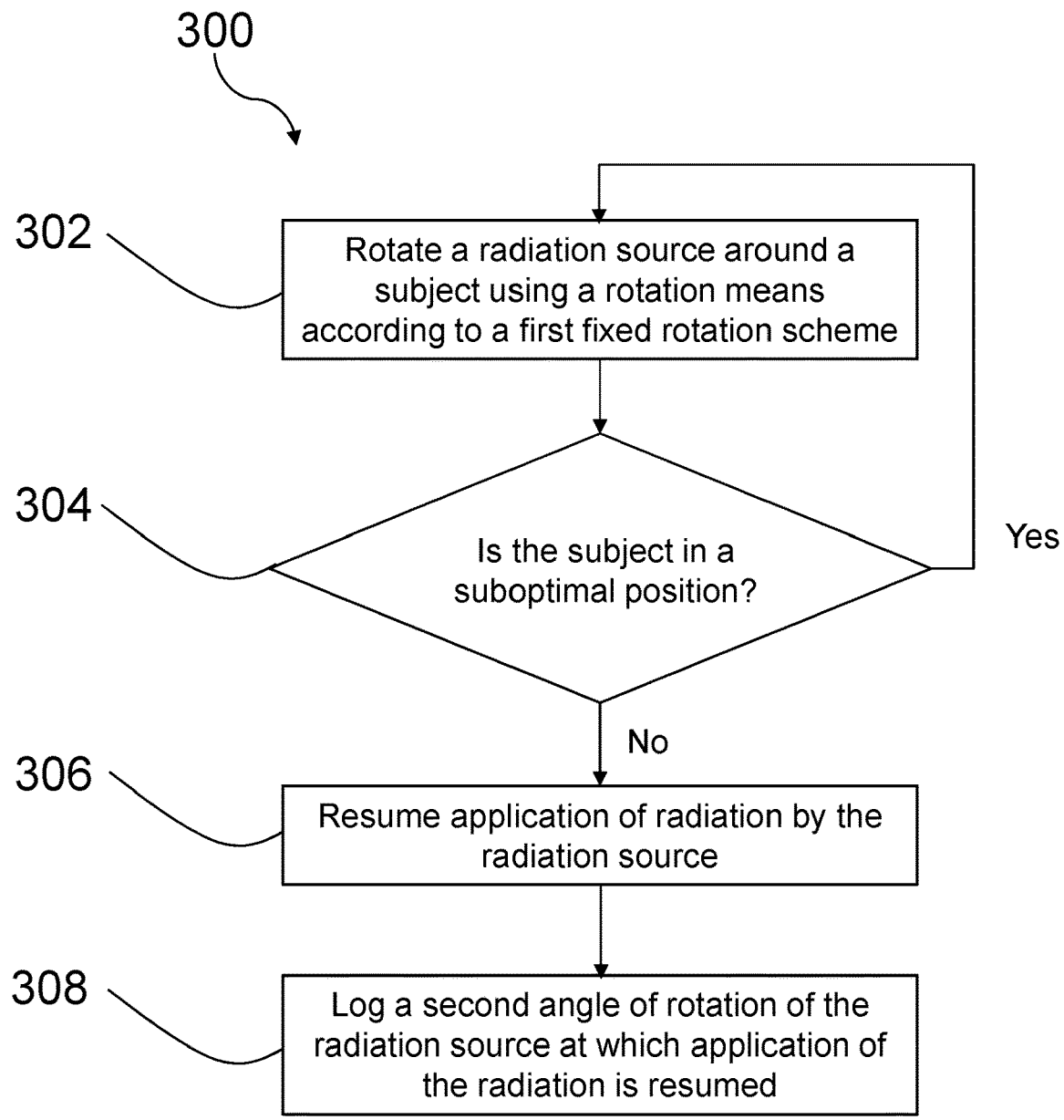
FIG. 4 depicts a further method of controlling a radiotherapy apparatus according to the present disclosure.

FIG. 4 depicts a further method 300 of controlling a radiotherapy device according to the present disclosure. The method depicted in FIG. 4 may take place after, for example immediately after, the method depicted in FIG. 3. The method depicted in FIG. 3 and the method depicted in FIG. 4 may take place during a treatment delivery. In some examples, the method depicted in FIG. 3 may occur in a treatment delivery without the method depicted in FIG. 4 and/or the method depicted in FIG. 4 may appear without the method depicted in FIG. 3. For example, a patient 108 may not enter a suboptimal position throughout a treatment delivery or may move to a suboptimal position during a treatment delivery and remain in the suboptimal position for the remainder of the treatment delivery.

In a step 302, rotation of the radiation source around a subject using the rotation means according to the first fixed rotation scheme may be continued. Step 302 may take place immediately after step 210 as described above. At the step 302, radiation may not be applied by the radiation source 100. In other words, at the step 302, the subject, e.g. a patient 108, may be in a suboptimal position.

In a step 304, a determination may be made as to whether the subject is in a suboptimal position. The determination may be performed using any of the means described above in relation to step 206. As described above, the term suboptimal should be interpreted as referring to a position of the patient 108 unsuitable for application of radiation using the radiation source 100. In other words, a suboptimal position should be interpreted as referring to a position that is not within a threshold of an ideal location. The threshold may be determined at least in part based on a spatial distribution of a target region, a spatial distribution of healthy tissue and/or a treatment plan.

If the result of the determination 304 is that the subject is in a suboptimal position, the method may return to step 302. If the result of the determination 304 is that the subject is not in a suboptimal position, the method may continue to step 306.

In the step 306, application of the radiation by the radiation source 100 may be resumed. In some examples, this application of the radiation by the radiation source 100 may be the first application of radiation by the radiation source in a particular treatment delivery. In such examples, it will be understood that the term resume may be understood as indicating the term begin. The resuming of the application of the radiation may be performed using gating of the radiation source 100, as described above.

In a step 308, a second angle of rotation of the radiation source 100 at which application of the radiation is resumed may be logged. The second angle of rotation may be logged in a log file. The first angle of rotation and/or the second angle of rotation may provide data indicating one or more time periods, and/or one or more angular ranges, during which radiation was applied to a subject. Alternatively, or in addition, the first angle or rotation and/or the second angle of rotation may provide data indicating one or more time periods, and/or one or more angular ranges, during which radiation was not applied to the subject.

While the method set out in FIG. 4 is presented in a certain sequential order, this should not be taken to limit the method to the order presented. The various steps may be performed in a different order. Various steps may be performed at the same time or substantially at the same time. For example, the steps of resuming 306 application of the radiation by the radiation source 100 and logging 308 a second angle of rotation of the radiation source 100, may be performed at the same time or substantially at the same time.

Figure 5:
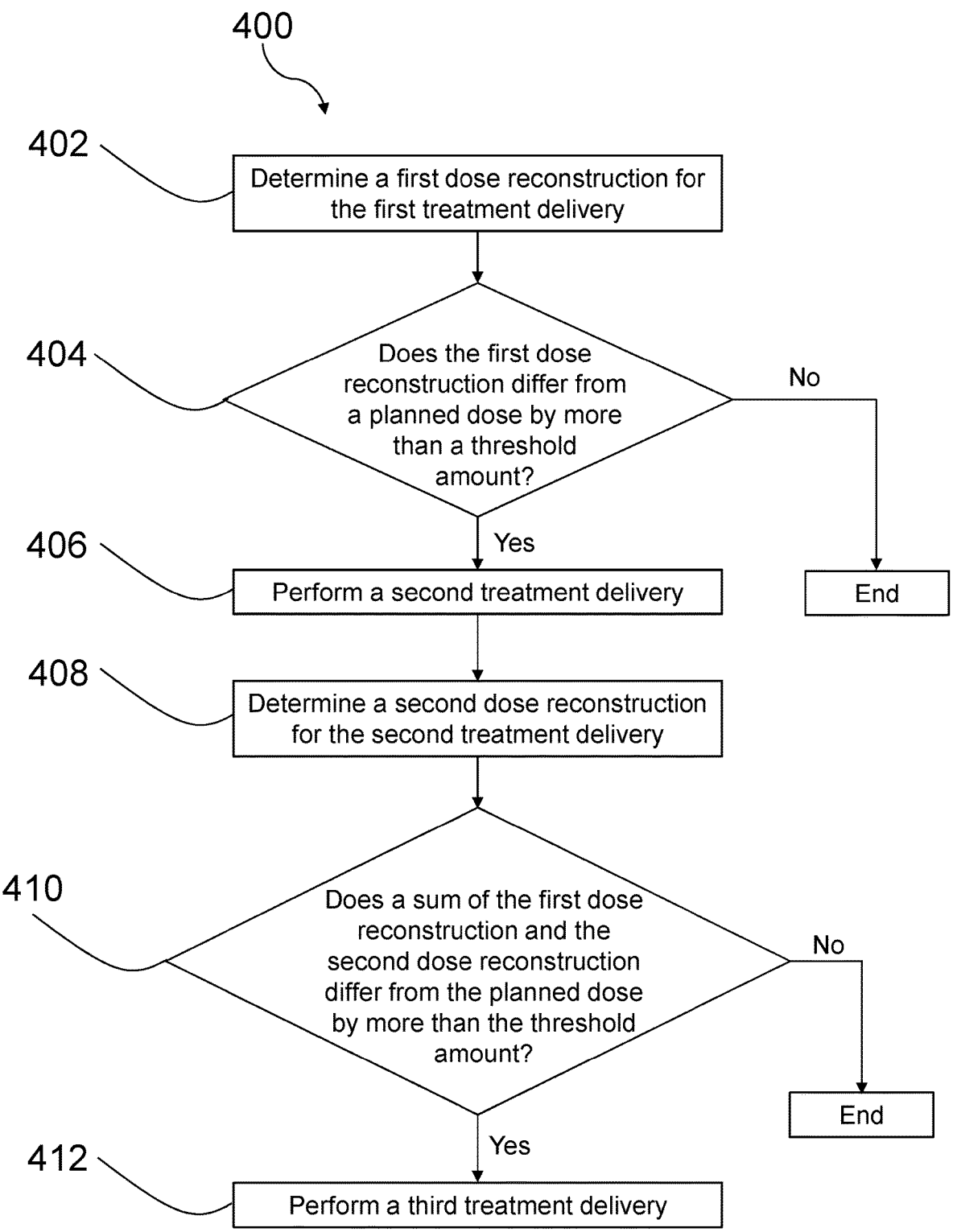
FIG. 5 depicts a further method of controlling a radiotherapy apparatus according to the present disclosure.

FIG. 5 depicts a further method 400 of controlling a radiotherapy device according to the present disclosure. The method depicted in FIG. 5 may occur at the end of a treatment delivery. For example, the method depicted in FIG. 5 may occur after the method depicted in FIG. 3 and/or the method depicted in FIG. 4.

In a step 402, a first dose reconstruction may be determined for the first treatment delivery. The first dose reconstruction may indicate a dose applied to a subject and/or a target region in the first treatment delivery. The first dose reconstruction may be determined based at least in part on the first angle of rotation and/or the second angle of rotation as described above, for example using the log file. In other words, the first dose reconstruction may be determined based on the range of angles of a treatment delivery for which radiation was applied by the radiation source 100 and/or the range of angles for a treatment delivery for which radiation was not applied by the radiation source 100. The first dose reconstruction may be based at least in part on a treatment plan. For example, the first dose reconstruction may be based at least in part on an intensity of the radiation applied and/or a speed or rate of rotation of the radiation source 100.

In a step 404, a determination may be made as to whether the first dose reconstruction differs from a planned dose by more than a threshold amount. The planned dose may be determined from or provided by the treatment plan. The threshold amount may be determined from or provided by the treatment plan. In some examples, the planned dose may correspond to a dose that would be received by a target region of the patient 108 during a treatment delivery if no motion or suboptimal positioning of the patient 108 were to occur. In these examples, if motion or suboptimal positioning of the patient 108 occurs, it will be appreciated that the first dose reconstruction at the target region may be less than the planned dose by a certain amount, which may or may not be greater than a threshold amount.

The reconstruction and/or the determination may be made using (online) gamma analysis or gamma index of the dose reconstruction against the treatment plan. Gamma analysis combines two parameters of quality assessment: a distance-to-agreement (DTA); and a dose difference (DD). The DTA may be defined as a nearest distance from a point of reference dose in the treatment plan to a point of the same dose in the dose reconstruction. The DD may be defined as a percentage difference between a dose to be applied according to the treatment plan and a dose applied according to the dose reconstruction. In Gamma analysis, the squares of the DTA and the DD may be summed, and the square root taken of this sum.

The determination of step 404 may be made with respect to a single spatial point and/or may be made with respect to a one, two or three-dimensional grid of spatial points corresponding to the target region and/or the healthy tissue of the subject. In this way, an absolute comparison and/or a spatially-resolved comparison may be made. In either case, the threshold amount may comprise a single value or may comprise a one, two or three-dimensional series or matrix of values for comparison to a difference between the dose reconstruction and the planned dose at each spatial point. For example, it may be more important to achieve a dose closer to a planned dose at a particular spatial location within a tumour, in which case the threshold at this particular spatial location may be smaller than at other spatial locations.

If the result of the determination 404 is that the first dose reconstruction does not differ from the planned dose by more than a threshold amount, the process may terminate. For example, a treatment of the subject or patient 108 may end for that day without a further treatment delivery being applied. If the result of the determination 406 is that the first dose reconstruction does differ from the planned dose by more than a threshold amount, the process may continue to step 406.

In the step 406, a second treatment delivery may be performed. The second treatment delivery may comprise at least rotating the radiation source 100 about the patient 108 using the rotation means and applying radiation to the patient 108 using the radiation source 100.

In other words, the second treatment delivery may be performed in a similar manner to the first treatment delivery. The second treatment delivery may comprise rotation according to a second fixed rotation scheme, which may be the same as or may differ from the first fixed rotation scheme. One or more angles may be logged in a similar manner as applies to the first treatment delivery. However, during the second treatment delivery, the radiation source 100 may apply radiation at or based on at least one angle at which radiation was not applied during the first treatment delivery. During the second treatment delivery, the radiation source 100 may not apply radiation at or based on at least one angle at which radiation was applied during the first treatment delivery. In this manner, the second treatment delivery may be used to compensate for incomplete application of radiation during a first treatment delivery. Parameters of the second treatment delivery may be determined based on data in the log file. In the second treatment delivery, the radiation source 100 may be gated to not apply radiation for angles at which adequate radiation has been applied to the patient 108, as determined based on the difference between the first dose reconstruction and the planned dose and in comparison with the threshold.

For quasiperiodic motion of a patient 108, such as due to breathing of the patient 108, if the second treatment delivery is begun at a same point in the quasiperiodic cycle as the first treatment delivery is begun, and if the speed of rotation used in the second treatment delivery is the same as used in the first treatment delivery, the separation distance of a target location within a subject and a radiation isocentre 112 may exceed a threshold distance $d_{th}$ at the same angle or angles in the second treatment delivery as occurred in the first treatment delivery. In this case, incomplete application of the planned dose in the first treatment delivery is not compensated for. In other words, if the quasiperiodic motion of the subject is in phase with the rotation of the radiation source 100, complete application of the planned dose may not be achieved, even with numerous further treatment deliveries. However, if the rotation of the radiation source 100 is configured to be out of phase, or in anti-phase, with the quasiperiodic motion of the subject, where there are angles of rotation for which the separation distance of the target location within the subject and the radiation isocentre 112 exceed a threshold distance du, for the first treatment delivery, these same angles of rotation may not correspond to separation distances that exceed the threshold distance for the second treatment delivery. Therefore, radiation may be applied by the radiation source 100 in the second treatment delivery at angles for which no radiation was applied by the radiation source 100 in the first treatment delivery. In this manner, a cumulative dose applied during the first treatment delivery and the second treatment delivery can be configured to correspond to a planned dose, within a threshold amount.

Configuring the rotation of the radiation source 100 to be out of phase, or in anti-phase, with the quasiperiodic motion of the subject, such as due to breathing of a patient 108, may be achieved in various ways. For example, a rate of rotation of the radiation source 100 during the second treatment delivery may be set based on the quasiperiodic motion, e.g. the breathing rate, of the patient 108. Alternatively, or in addition, an interval between a first end time of the first treatment delivery and a second start time of the second treatment delivery may be defined based on the quasiperiodic motion, e.g. the breathing rate, of the patient 108. In some examples, a signal indicating a certain point of a cycle of quasiperiodic motion of the patient 108 may trigger a start of the second treatment delivery at the second start time.

In a step 408, a second dose reconstruction may be determined for the second treatment delivery. The second dose reconstruction may be determined in a similar manner to the first dose reconstruction, except in that the second dose reconstruction is determined based on data, e.g. one or more angles, corresponding to the second treatment delivery.

In a step 410, a determination is made as to whether a sum of the first dose reconstruction and the second dose reconstruction differs from the planned dose by more than the threshold amount. In other words, a determination is made as to whether the second treatment delivery has adequately compensated for incomplete application of the planned dose during the first treatment delivery. As described above, the determination may be made, and the threshold amount may be defined, in an absolute manner or in a spatially resolved manner.

If the result of the determination 410 is that the sum of the first dose reconstruction and the second dose reconstruction does not differ from the planned dose by more than the threshold amount, the process may terminate. For example, a treatment of the patient 108 may end for that day without a further treatment delivery being applied. If the result of the determination 410 is that the sum of the first dose reconstruction and the second dose reconstruction does differ from the planned dose by more than a threshold amount, the process may continue to step 412.

It is anticipated that, due to the consideration of the phases of the quasiperiodic motion of the subject and the rotation of the radiation source 100, the steps described above will be adequate for achieving a total applied dose close to a planned dose where the deviation of the first dose reconstruction from the planned dose was due to quasiperiodic motion of the subject. However, particularly in cases where further motion of the subject occurs, for example due to coughing or sneezing of a patient 108, one or more further treatment deliveries may be performed.

In a step 412, a third treatment delivery may be performed. The third treatment delivery may be performed in a similar manner to the second treatment delivery. However, during the third treatment delivery, the radiation source 100 may apply radiation at or based on at least one angle at which radiation was not applied during either of the first treatment delivery and the second treatment delivery. During the third treatment delivery, the radiation source 100 may not apply radiation at or based on at least one angle at which radiation was applied during either of the first treatment delivery and the second treatment delivery. In this manner, the third treatment delivery may be used to compensate for incomplete application of radiation during the first treatment delivery and the second treatment delivery.

It will be appreciated that further dose reconstructions, determinations and treatment deliveries may be performed in a similar manner to those described above, for example until a sum of dose reconstructions differs from a planned dose by less than the threshold amount. In some examples, the number of treatment deliveries performed may be limited based on cumulative doses applied to healthy tissue, for example to ensure safety of a patient 108, or based on time constraints.

In some examples, adaptive radiotherapy (ART) may be used to vary the planned dose and/or the treatment plan during or between treatment deliveries. Such variation may be based on real-time measurements of patient anatomy during a treatment delivery (for example using MR imaging) and/or based on post-treatment measurements. This may be used to account for changes occurring to a patient 108, for example to a target region, during a radiotherapy treatment relative to the patient/target region when the initial treatment plan was formulated. It may also be used to take into account uncertainties in the patient 108 setup or the radiotherapy device 120 setup. In these examples, references to the planned dose in the context of the methods described herein may be taken to be references to a planned dose as updated. The planned dose as updated may be based on the planned dose and the measurements described above. The planned dose may be updated continuously or at intervals or at pre-defined points. For example, it may be determined whether the first dose reconstruction differs from the planned dose as updated by more than a threshold amount, whether the sum of the first dose reconstruction and the second dose reconstruction differs from the planned dose as updated by more than the threshold amount, and/or whether sums of further dose reconstructions differ from the planned dose as updated by more than a threshold amount.

Figure 6:
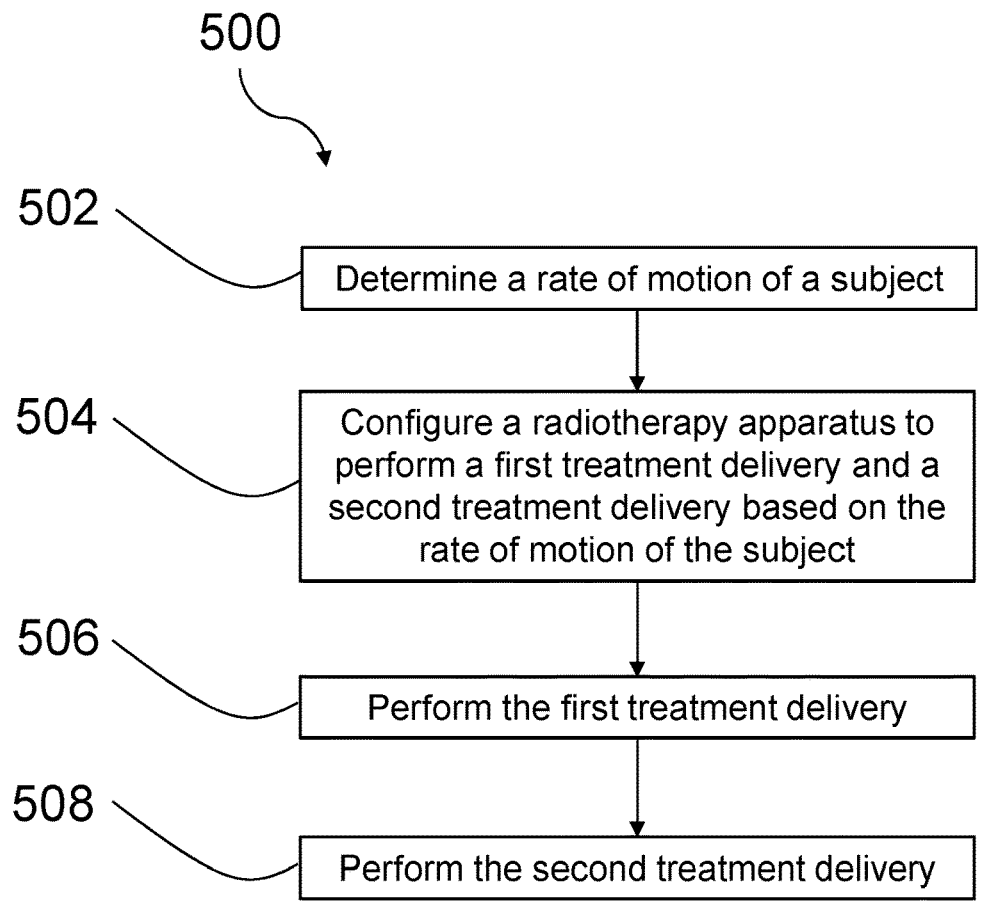
FIG. 6 depicts a further method of controlling a radiotherapy apparatus according to the present disclosure.

FIG. 6 depicts a further method 500 of controlling a radiotherapy apparatus according to the present disclosure.

In a step 502, a determination may be made of a rate of motion of a subject. The motion may be quasiperiodic motion, for example due to breathing of a patient 108. The determination may be made based on any one or combination of suitable means, including but not limited to one or more cameras, movement sensors, accelerometers, chest bands, a button to pressed by the patient 108 and an MR imaging device. Use of more than one of these means may be combined. Such merging of multiple data streams can improve accuracy and/or robustness. The rate of motion may be logged, for example in a log file.

In a step 504, a radiotherapy apparatus may be configured to perform a first treatment delivery and a second treatment delivery based on the rate of motion of the subject. The first treatment delivery may comprise a first fixed rotation scheme. The second treatment delivery may comprise a second fixed rotation scheme. For example, the radiotherapy apparatus may be configured such that a cumulative dose applied during the first treatment delivery and the second treatment delivery corresponds to a planned dose within a threshold amount. For example, a rotation or rotation rate of the radiation source in the first treatment delivery and/or in the second treatment delivery may be controlled to be out of phase, for example in anti-phase, with the motion of the subject. Alternatively, or in addition, a time interval between a first end time of the first treatment delivery and a second start time of the second treatment delivery may be configured such that the start of the second treatment delivery corresponds to a second point in the cycle of motion of the subject that is different to a first point in the cycle of motion corresponding to the start of the first treatment delivery. In other words, the second point may be dissimilar to the first point in that it occurs at a different stage in the cycle of motion of the subject. For example, the first point and the second point may be separated by a non-integer number of wavelengths of the cycle of motion of the subject. In this manner, the second treatment delivery may be commenced at a time such that the second treatment delivery may compensate for incomplete application of a planned dose during a first treatment delivery.

In a step 506, the first treatment delivery is performed as configured in step 504.

In a step 508, the second treatment delivery is performed as configured in step 504.

The approaches described herein may be embodied on a computer-readable medium, which may be a non-transitory computer-readable medium. The computer-readable medium may carry computer-readable instructions arranged for execution upon a processor so as to make the processor carry out any or all of the methods described herein.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. A computer implemented method of controlling a radiotherapy device, the radiotherapy device comprising a radiation source coupled to a rotation member, the method comprising:
    applying radiation to a subject using the radiation source;
    rotating the radiation source around the subject using the rotation member according to a first fixed rotation scheme; and
    during execution of the first fixed rotation scheme:
        determining that the subject is in a suboptimal position;
        pausing application of the radiation by the radiation source in response to determining that the subject is in the suboptimal position; and
        logging a first angle of rotation of the radiation source at which application of the radiation is paused, wherein at least one of a speed of rotation of the radiation source or a start time at which the radiation source is to start to rotate is set based on at least one of: i) a signal comprising movement data for the subject, or ii) a signal comprising breathing data for the subject.

2. The method of claim 1, further comprising:
    during execution of the first fixed rotation scheme:
        determining that the subject is not in a suboptimal position;
        resuming application of the radiation by the radiation source in response to the determining that the subject is not in a suboptimal position; and
        logging a second angle of rotation of the radiation source at which application of the radiation is resumed.

3. The method of claim 2, wherein a first treatment delivery comprises:
    rotating the radiation source around the subject using the rotation member according to the first fixed rotation scheme;
    applying the radiation to the subject using the radiation source; and
    at a first end time at which the first treatment delivery has completed, determining a first dose reconstruction for the first treatment delivery based at least in part on the first angle of rotation.

4. The method of claim 3, further comprising:
    determining whether the first dose reconstruction differs from a planned dose by more than a threshold amount.

5. The method of claim 4, wherein the planned dose is updated based on one or more measurements taken during and/or after the first treatment delivery, wherein the determining whether the first dose reconstruction differs from the planned dose by more than the threshold amount comprises determining if the first dose reconstruction differs from the planned dose as updated by more than the threshold amount.

6. The method of claim 4, comprising, in response to a determination that the first dose reconstruction differs from the planned dose by more than the threshold amount, performing a second treatment delivery, the second treatment delivery comprising:
    applying radiation to the subject using the radiation source; and
    rotating the radiation source around the subject using the rotation member according to a second fixed rotation scheme.

7. The method of claim 6, wherein the applying the radiation to the subject using the radiation source during the second treatment delivery comprises:
    applying the radiation at or based on the first angle of rotation.

8. The method of claim 6, wherein the applying the radiation to the subject using the radiation source during the second treatment delivery comprises:
    not applying the radiation at or based on the second angle of rotation.

9. The method of claim 6, further comprising:
    determining, at a second end time at which the second treatment delivery has completed, a second dose reconstruction for the second treatment delivery.

10. The method of claim 9, further comprising:
    determining whether a sum of the first dose reconstruction and the second dose reconstruction differs from the planned dose by more than the threshold amount.

11. The method of claim 1, further comprising execution of a treatment plan, the treatment plan comprising:
    a first treatment delivery, comprising rotating the radiation source around the subject using the rotation member according to the first fixed rotation scheme, and applying radiation to the subject using the radiation source; and a second treatment delivery, comprising rotating the radiation source around the subject using the rotation member according to a second fixed rotation scheme, and applying radiation to the subject using the radiation source.

12. The method of claim 11, wherein the treatment plan comprises at least one of a first rotation rate of the radiation source during the first treatment delivery, the first rotation rate being determined based on the signal comprising movement data for the subject, or a second rotation rate of the radiation source during the second treatment delivery, the second rotation rate being determined based on the signal comprising movement data for the subject.

13. The method of claim 11, wherein the treatment plan comprises a time interval between a first end time of the first treatment delivery and a second start time of the second treatment delivery, the time interval being determined based on the signal comprising movement data for the subject.

14. The method of claim 11, wherein rotation of the radiation source is controlled to be out of phase with motion of the subject or is controlled to be in anti-phase with the motion of the subject.

15. The method of claim 1, wherein the determining that the subject is in a suboptimal position is based on a signal comprising movement data for the subject or on the signal comprising breathing data for the subject.

16. The method of claim 1, wherein a speed of rotation of the radiation source is set based on at least one of a signal comprising movement data for the subject, a signal comprising breathing data for the subject, or wherein a start time at which the radiation source starts to rotate is set based on at least one of a signal comprising movement data for the subject or a signal comprising breathing data for the subject.

17. The method of claim 11, wherein the radiation source rotates substantially continuously during at least one of the first treatment delivery or the second treatment delivery.

18. The method of claim 2, wherein the logging the first angle of rotation of the radiation source comprises logging the first angle of rotation of the radiation source in a log file and/or wherein the logging the second angle of rotation of the radiation source comprises logging the second angle of rotation of the radiation source in a log file.

19. A computer readable medium comprising computer executable instructions which, when executed by a processor, cause a radiotherapy device comprising a radiation source coupled to a rotation member to:

apply radiation to a subject using the radiation source;
rotate the radiation source around the subject using the rotation member according to a first fixed rotation scheme; and
during execution of the first fixed rotation scheme:
determine that the subject is in a suboptimal position;
pause application of the radiation by the radiation source in response to the determination that the subject is in the suboptimal position; and
log a first angle of rotation of the radiation source at which application of the radiation is paused, wherein at least one of a speed of rotation of the radiation source or a start time at which the radiation source is to start to rotate is set based on at least one of: i) a signal comprising movement data for the subject, or ii) a signal comprising breathing data for the subject.

20. A radiotherapy device comprising a radiation source coupled to a rotation member, the radiotherapy device being configured to:

apply radiation to a subject using the radiation source;
rotate the radiation source around the subject using the rotation member according to a first fixed rotation scheme; and
during execution of the first fixed rotation scheme:
determine that the subject is in a suboptimal position;
pause application of the radiation by the radiation source in response to the determination that the subject is in the suboptimal position; and
log a first angle of rotation of the radiation source at which application of the radiation is paused, wherein at least one of a speed of rotation of the radiation source or a start time at which the radiation source is to start to rotate is set based on at least one of: i) a signal comprising movement data for the subject, or ii) a signal comprising breathing data for the subject.

* * * * *